(12) United States Patent
Danehorn

(10) Patent No.: US 8,825,134 B2
(45) Date of Patent: *Sep. 2, 2014

(54) CATHETER LOCALIZATION SYSTEM

(75) Inventor: Kenneth Danehorn, Vaxholm (SE)

(73) Assignee: Siemens Aktiengesellschaft, Munich (DE)

( * ) Notice: Subject to any disclaimer, the term of this patent is extended or adjusted under 35 U.S.C. 154(b) by 1232 days.

This patent is subject to a terminal disclaimer.

(21) Appl. No.: 11/855,737

(22) Filed: Sep. 14, 2007

(65) Prior Publication Data

US 2009/0076483 A1    Mar. 19, 2009

(51) Int. Cl.
  *A61B 5/05* (2006.01)
  *A61B 19/00* (2006.01)
  *A61M 25/01* (2006.01)

(52) U.S. Cl.
  CPC ........ *A61M 25/01* (2013.01); *A61B 2019/5253* (2013.01); *A61M 2025/0166* (2013.01); *A61B 19/5244* (2013.01); *A61B 2019/5251* (2013.01)
  USPC ............ 600/424; 600/373; 600/374; 600/429

(58) Field of Classification Search
  USPC ................ 600/382, 373, 424, 547; 128/899; 129/899
  See application file for complete search history.

(56) References Cited

U.S. PATENT DOCUMENTS

| | | | | | |
|---|---|---|---|---|---|
| 5,042,486 | A | * | 8/1991 | Pfeiler et al. | 600/424 |
| 5,391,199 | A | * | 2/1995 | Ben-Haim | 607/122 |
| 5,398,691 | A | * | 3/1995 | Martin et al. | 600/463 |
| 5,443,489 | A | * | 8/1995 | Ben-Haim | 607/115 |
| 5,687,737 | A | * | 11/1997 | Branham et al. | 600/523 |
| 5,697,377 | A | * | 12/1997 | Wittkampf | 600/374 |
| 5,830,145 | A | * | 11/1998 | Tenhoff | 600/463 |
| 5,840,031 | A | * | 11/1998 | Crowley | 600/440 |
| 5,876,345 | A | * | 3/1999 | Eaton et al. | 600/466 |
| 5,879,305 | A | * | 3/1999 | Yock et al. | 600/462 |
| 5,944,022 | A | * | 8/1999 | Nardella et al. | 128/899 |
| 6,049,732 | A | * | 4/2000 | Panescu et al. | 600/523 |
| 6,050,267 | A | * | 4/2000 | Nardella et al. | 128/899 |
| 6,171,303 | B1 | * | 1/2001 | Ben-Haim et al. | 606/15 |
| 6,216,027 | B1 | * | 4/2001 | Willis et al. | 600/424 |
| 6,230,042 | B1 | * | 5/2001 | Slettenmark | 600/424 |
| 6,246,898 | B1 | * | 6/2001 | Vesely et al. | 600/424 |
| 6,259,941 | B1 | * | 7/2001 | Chia et al. | 600/424 |
| 6,385,476 | B1 | * | 5/2002 | Osadchy et al. | 600/407 |
| 6,468,265 | B1 | * | 10/2002 | Evans et al. | 606/1 |
| 6,490,474 | B1 | * | 12/2002 | Willis et al. | 600/424 |
| 6,546,270 | B1 | * | 4/2003 | Goldin et al. | 600/374 |
| 6,574,492 | B1 | * | 6/2003 | Ben-Haim et al. | 600/374 |
| 6,612,992 | B1 | * | 9/2003 | Hossack et al. | 600/467 |
| 6,807,439 | B2 | * | 10/2004 | Edwards et al. | 600/420 |
| 6,858,003 | B2 | * | 2/2005 | Evans et al. | 600/103 |

(Continued)

OTHER PUBLICATIONS

U.S. Appl. No. 11/820,697, Danehorn.

*Primary Examiner* — Nicholas Evoy

(74) *Attorney, Agent, or Firm* — Lempia Summerfield Katz LLC

(57) ABSTRACT

A system and method for localizing a catheter is provided. Distance values are determined between a plurality of reference electrodes and a catheter electrode. At least two circles are identified based on the distance values. The catheter electrode is located at a position where the at least two circles substantially coincide or within a minimum distance between the at least two circles. A transformation is applied to the at least two circles to express the at least two circles in a global coordinate system. An image is displayed as a function of the catheter electrode position.

23 Claims, 6 Drawing Sheets

(56) References Cited

U.S. PATENT DOCUMENTS

| | | | |
|---|---|---|---|
| 6,970,733 B2* | 11/2005 | Willis et al. | 600/424 |
| 7,019,650 B2* | 3/2006 | Volpi et al. | 340/572.1 |
| 7,263,397 B2* | 8/2007 | Hauck et al. | 600/374 |
| 7,756,576 B2* | 7/2010 | Levin | 600/547 |
| 2003/0036696 A1* | 2/2003 | Willis et al. | 600/424 |
| 2003/0050557 A1* | 3/2003 | Susil et al. | 600/424 |
| 2003/0055410 A1* | 3/2003 | Evans et al. | 606/1 |
| 2004/0054248 A1* | 3/2004 | Kimchy et al. | 600/3 |
| 2005/0033281 A1* | 2/2005 | Bowman et al. | 606/41 |
| 2005/0090870 A1 | 4/2005 | Hine et al. | |
| 2006/0084867 A1* | 4/2006 | Tremblay et al. | 600/434 |
| 2007/0066889 A1* | 3/2007 | Boese et al. | 600/424 |
| 2007/0078334 A1* | 4/2007 | Scully et al. | 600/424 |
| 2007/0083247 A1* | 4/2007 | Wyeth et al. | 607/99 |
| 2007/0135803 A1* | 6/2007 | Belson | 606/1 |
| 2008/0190438 A1* | 8/2008 | Harlev et al. | 128/898 |

\* cited by examiner

CATHETER LOCALIZATION SYSTEM

BACKGROUND

The present embodiments relate to medical catheters. In particular, accurate positioning of a catheter inside a body using electrodes is provided.

Catheters are used for several types of medical procedures. For example, catheters are used to measure electrical activity, capture image data, and/or apply stents within a body. Additionally, catheters are used for ablation therapy, especially for the treatment of heart disease. The positioning of such catheters during treatment or measurement procedures is of great interest to medical professionals due to the limited area to navigate within or due to navigation near sensitive internal organs.

A variety of medical imaging systems are used to assist medical professionals with maneuvering and positioning catheters within a body. For example, ultrasound, computed tomography ("CT"), and X-ray systems are used to generate images of the catheter within the body during treatment or measurement procedures. However, minimizing the use of imaging systems during the catheter procedures may be desired to reduce cost as well as minimize exposure, such a X-rays, to the patient.

Catheter positioning systems may not utilize external medical imaging systems during the entire treatment or measurement procedures. Specialized catheters having coils or transducers or systems utilizing patches positioned along three mutually orthogonal axes on a body surface have been proposed. However, the use of such systems may increase cost as well as complexity.

BRIEF SUMMARY

By way of introduction, the preferred embodiments described below include catheters including electrodes, body surface electrodes, and methods of positioning a catheter within a body. A plurality of reference electrodes are provided. A catheter having an electrode is operable to communicate with the reference electrodes, and a position of the catheter is determined based on the communication between the electrodes.

According to a first aspect, a method for localizing a catheter is provided. Distance values are determined between a plurality of reference electrodes and a catheter electrode. At least two circles are identified based on the distance values. The catheter electrode is located at a position where the at least two circles substantially coincide or within a minimum distance between the at least two circles. A transformation is applied to the at least two circles to express the at least two circles in a global coordinate system. An image is displayed as a function of the catheter electrode position.

According to a second aspect, a system for localizing a catheter is provided. An electrode is on a catheter. A plurality of reference electrodes are provided. Each of the plurality of reference electrodes are configured to transmit or receive a signal to or from the electrode, respectively. A processor is operable to determine distance values between the plurality of reference electrodes and the electrode. The processor is further operable to determine a position of the electrode with at least two circles based on the distance values and applying a transformation to the at least two circles.

According to a third aspect, a computer-readable medium has stored therein instructions executable by a processor. The instructions comprise determining distance values between a plurality of reference electrodes and a catheter electrode. At least two circles are determined based on the distance values. The catheter electrode is located at a position where the at least two circles are the closest. A transformation is applied to the at least two circles. The transformed at least two circles are in a global coordinate system.

The present invention is defined by the following claims, and nothing in this section should be taken as a limitation on those claims. Further aspects and advantages of the invention are discussed below in conjunction with the preferred embodiments.

BRIEF DESCRIPTION OF THE DRAWINGS

The components and the figures are not necessarily to scale, emphasis instead being placed upon illustrating the principles of the invention. Moreover, in the figures, like reference numerals designate corresponding parts throughout the different views.

DETAILED DESCRIPTION OF THE DRAWINGS AND PRESENTLY PREFERRED EMBODIMENTS

The embodiments entail a system and method of determining a position of a catheter using electrodes as well as a transformation technique for localizing the catheter. The system and method may utilize standard triangulation calculations to determine the position of the catheter. As an alternative, the system and method implements the transformation technique described below to determine accurate position of the catheter. FIGS. 1-5 and 9 are used to describe the system and method of determining a position of the catheter, and FIGS. 6-8 focus on the transformation technique for localizing the catheter.

A position of a treatment and/or measurement catheter having electrodes can be determined in a two step approach. Firstly, relative distances between reference body surface electrodes or electrodes on a reference catheter and the electrodes on the treatment and/or measurement catheter are calibrated by image segmentation using X-ray images. Secondly, distances between the treatment and/or measurement catheter and the reference catheter or reference body surface electrodes are measured by estimating the impedance of blood between the electrodes or measuring the voltage potential between non-transmitting or non-receiving electrodes. Several reference catheters and/or reference body surface electrodes can be used to obtain more accurate positioning information. The accurate position of electrodes in the measurement and/or treatment catheter is measured either in a sequential manner or using signals with different frequencies, and the accurate position is derived using triangulation methods. Alternatively, transformation methods or calculations may be used to derive the accurate position. Also, heart beat motion and breathing motion can be compensated for by various triggering techniques. Coordinate position data gathered by the system may be used in conjunction with an image volume data set to enable a three dimensional ("3D") animation of the measurement and/or treatment catheter within a body.

Figure 1:
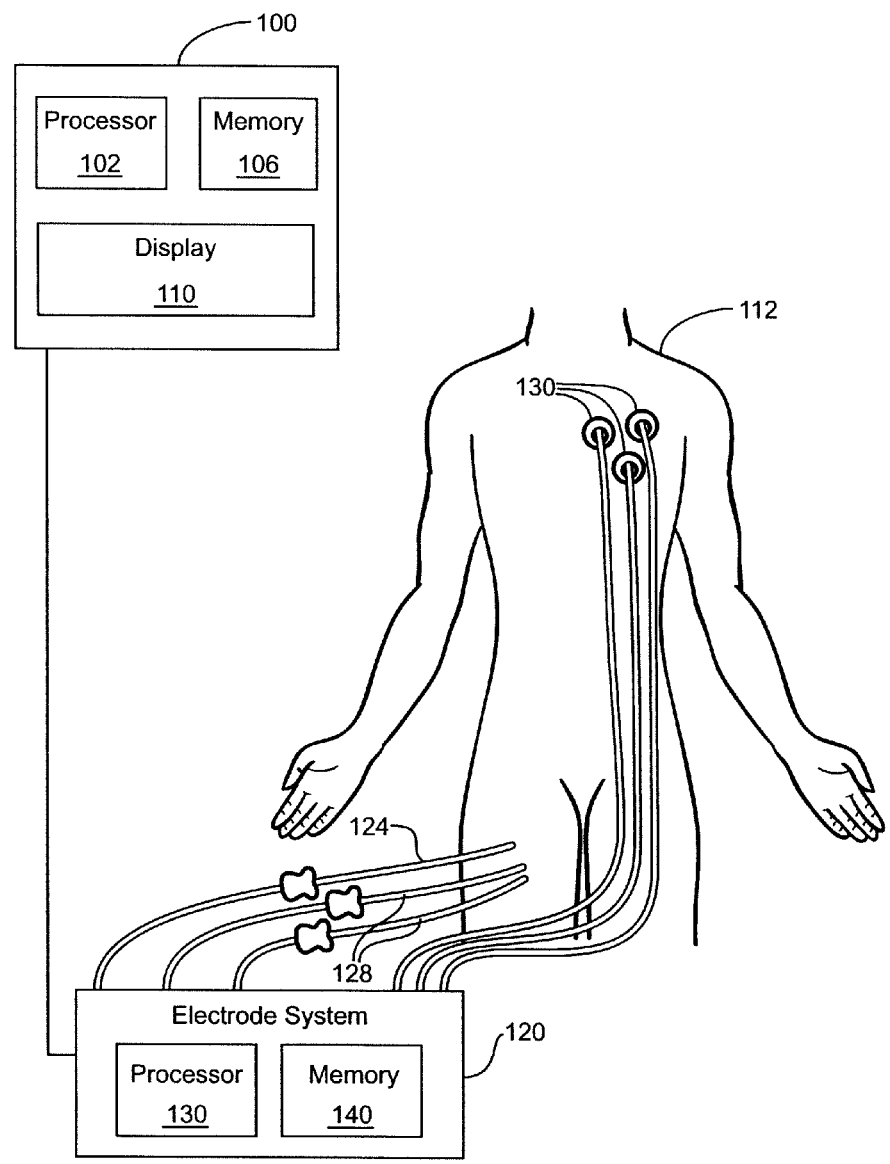
FIG. 1 is a general diagram illustrating one embodiment of a system for determining a position of a catheter.

FIG. 1 is a general diagram illustrating one embodiment of a system for determining a position of a catheter 124. The system includes, but is not limited to an imaging system 100, an electrode system 120, a catheter 124, reference catheters 128, and reference body surface electrodes 130. Fewer or more components may be utilized.

The imaging system 100 is a X-ray system, CT system, ultrasound system, or any known or future medical imaging system. For example, the imaging system 100 is a X-ray system operable to generate X-ray images of a chest region of a patient 112. The imaging system 100 includes a processor 102, a memory 106, a display 110, and/or any known or future electronic and/or audio/visual hardware used for medical imaging.

The processor 102 is in communication with the memory 106 and the display 110. The processor 102 is a main processor, such as a microprocessor, or a plurality of processors operable to communicate with electronics of the imaging system 100. The memory 106 is any known or future storage device. For example, the memory 106 is a non-volatile and/or volatile memory, such as a Random Access Memory "RAM" (electronic), a Read-Only Memory "ROM" (electronic), or an Erasable Programmable Read-Only Memory (EPROM or Flash memory). The display 110 is any mechanical and/or electronic display positioned for accessible viewing by a doctor or medical professional. For example, the display 110 is a liquid crystal display, ("LCD"), printer, or cathode ray tube ("CRT") monitor. The display 110 is operable to show 2D, 3D, and/or four dimensional ("4D") images (i.e., the fourth dimension is time, and, therefore, 4D images are a sequence of images that show an object over a time period).

The imaging system 100 is operable to process or run any variety of known of future medical imaging software protocols and/or applications. For example, the imaging system 100 includes or is operable to load programs or applications for determining calibration position data for the catheter 124 within the patient 112 as well as for processing image data and rendering 2D, 3D, and/or 4D images.

The electrode system 120 is in communication with the imaging system 100. The electrode system 120 includes, but is not limited to, a processor 130 and a memory 140. The processor 130 is in communication with the processor 130. The processor 130 is a main processor, such as a microprocessor, or a plurality of processors operable to communicate with electronics of the electrode system 120. The memory 140 is any known or future storage device. For example, the memory 140 is a non-volatile and/or volatile memory, such as a Random Access Memory "RAM" (electronic), a Read-Only Memory "ROM" (electronic), or an Erasable Programmable Read-Only Memory (EPROM or Flash memory).

The electrode system 120 is operable to receive calibration data from the imaging system 100 and to process electrical signals from the catheter 124, the reference catheters 128, and/or the body surface electrodes 130 to determine an internal position of the catheter 124. Additionally, the electrode system 120 may transmit the catheter 124 position data to the imaging system 100 to display a 3D animation or virtual image of the catheter inside the patient 112.

Alternatively, the imaging system 100 and the electrode system 120 are one system. Or, the imaging system 100 and the electrode system 120 are separate systems that are not in communication with each other. In this case, calibration data acquired by the imaging system 100 is transferred or entered into the electrode system 120, and position data of the catheter 124 determined by the electrode system 120 is used to display an image of the catheter 124 on a display connected with the electrode system 120, the imaging system 100, or another imaging system. Any combination of features and components of the imaging system 100 and the electrode system 120 may combined or separated in one or more systems.

The patient 112 is any living or nonliving object. For example, the patient 112 is an animal or human being. The catheter 124 and the catheters 128 are inserted through any part or region of the patient 112 to be positioned in or by any anatomical feature for treatment and/or measurement purposes. For example, to measure heart activity or to perform ablation therapy on the heart of the patient 112, the catheter 124 and the reference catheters 128 are inserted into a limb, such as an arm or leg, of the patient 112 to enter into a vein or artery that leads to the heart. For example, the catheter 124 is inserted into a femoral vein of the patient 120. The reference catheters 128 may be inserted into the same vein or other veins. Alternatively, the catheter 124 and the reference catheters 128 are inserted in the throat, chest, abdomen, any opening or orifice, or any other part of the patient 112. The body surface electrodes 130 may be attached to any part of the patient 112's body in conjunction with the catheter 124 and the reference catheters 128. For example, the body surface electrodes 130 are attached on the chest of the patient 112. The body surface electrodes 130 may be positioned at specific locations, such as at a particular distance and direction from the naval and/or nipples.

Figure 2:
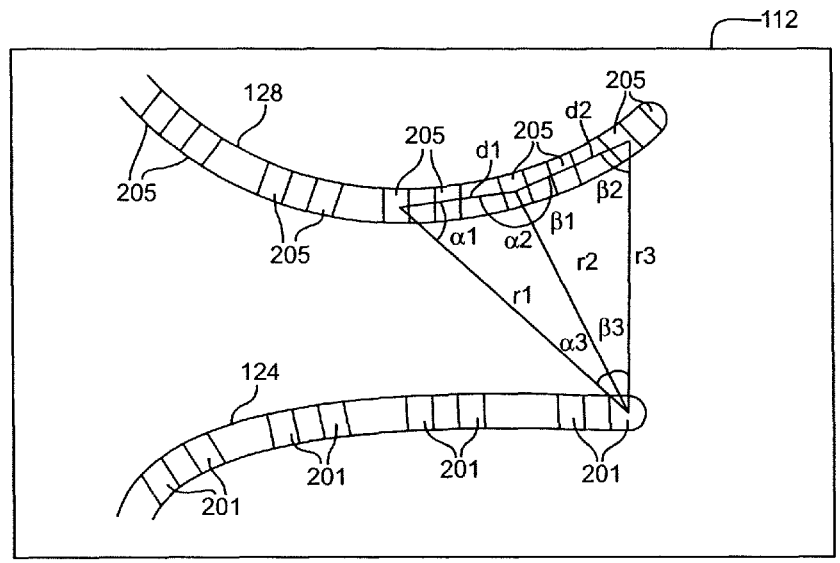
FIG. 2 is a magnified view of one embodiment of the system for determining a position of a catheter of FIG. 1.

Referring to FIG. 2, the catheter 124 is a treatment catheter used for ablation therapy or applying stents, a measurement catheter used for measuring electrical or other physiological activity, an imaging catheter, such as an ultrasonic catheter, and/or any other known or future catheter. For example, the catheter 124 includes a body or lumen having a longitudinal axis and a circumference. The body or lumen is a flexible shaft that is made of a plastic, a polymer, and/or any known or future flexible material. The lumen is sized for insertion into the circulatory system, such as less than about 5 mm in diameter. The body may include a flexible tip and/or guide wires. Also, the catheter 124 may include a handle and/or a steering mechanism.

Pairs of electrodes 201 are disposed on or in the body of the catheter 124. Alternatively, the electrodes 201 may be disposed in non-pair configurations. The electrodes 201 are disposed spaced apart from the distal end of the catheter 124 to any predetermined position along the length of the body of the catheter 124. The electrodes 201 form a continuous or non-continuous loop around the body of the catheter 124 allowing contact with blood or tissue within the patient 112. Alternatively, predetermined grooves may be set in the outer surface of the catheter 124 to receive the electrodes 201 so that the electrodes 201 are flush with the rest of the outer surface of the catheter 124. The electrodes 201 are made of any metal material or any known or future material operable to transmit and receive electrical signals. Alternatively, the electrodes 201 are made of a non-magnetic material that may be scanned with a magnetic resonance imaging ("MRI") system and yet still transmit and receive electrical signals. The electrodes 201 are connected with the electrode system 120. The electrodes 201 are also connected with a voltage or current generator, which may or may not be part of the electrode system 120. The generator is connected with all or some of the electrodes 201. For example, the generator is connected to one electrode 201 in each pair of the electrodes 201. The generator may be connected to one electrode 201 in the most distal pair, the most proximal pair, and a middle pair of electrodes 201.

The reference catheter 128 is a catheter for transmitting and receiving electrical signals. For example, the reference catheter 128 includes a body or lumen having a longitudinal axis and a circumference. The body or lumen is a flexible shaft that is made of a plastic, a polymer, and/or any known or future flexible material. For example, the body of the reference catheter 128 has a curvilinear shape. Also, the reference catheter 128 may include a handle and/or a steering mechanism.

Electrodes 205 are disposed on the body of the reference catheter 128. The arrangement and type of the electrodes 205 are similar to or the same as the electrodes 201, as described above. Different arrangements and/or type may be used. The electrodes 205 are not positioned on or in the body surface of the patient 112 along three mutually orthogonal axes. The electrodes 205 are connected with the electrode system 120. The electrodes 205 are also connected with a voltage or current generator, which may or may not be part of the electrode system 120. The voltage or current generator may be the same generator used in conjunction with the catheter 124 or may be a separate generator. The respective generator is connected with all or some of the electrodes 205.

For example, the voltage or current generator for the catheter 124 generates an alternating current ("AC") signal, such as a low current signal at about 10 kHz, and transmits the signal from one electrode 201, and the voltage or current generator for the reference catheter 128 generates a signal at substantially the same frequency with a phase shift of 180 degrees and transmits that signal from one electrode 205. By having a 180 degree phase shift, a current is created between the electrode 201 and the electrode 205. To insure that the current is floating from the electrode 201 and the electrode 205, these electrodes are controlled to have low impedance in relation to the other electrodes. This is accomplished by phase shifting two generators connected to the electrode 201 and the electrode 205, respectively. The phase shifting acts as a current pump where electrons are pumped from one electrode to another electrode. A current may be generated between any of the electrodes 201 and 205, respectively. This transmitting and receiving configuration between the electrodes 201 and 205 is time divided so that one frequency is used. Alternatively, the same voltage or signal generator is used for both the electrodes 201 and 205. Or, separate voltage or current generators are used for each or a group of electrodes 201 and 205 to allow for the use of different frequencies without sequentially transmitting or receiving signals between the electrodes 201 and 205.

Also, a direct current ("DC") signal may be used between the electrodes 201 and 205. For example, DC generators connected with the catheter 124 and the reference catheter 128 may allocate specific sinking and sourcing timing configurations to allow for a DC current between a certain electrode 201 and a certain electrode 205.

A position of an electrode 201 is determined based on an electrical characteristic of the signal between the electrode 201 and a respective electrode 205. For example, an impedance of blood between the electrode 201 and the electrode 205 is calculated using any known or future mathematics or physics calculation or equation, such as Ohms' law. The different impedances between electrodes relate to the distances between the same electrodes. For example, the impedance will increase as the distance between electrodes increases. A predetermined look-up table may be used to store distance values that correlate to different impedances. These values may be obtained by testing the patient 112 or other patients. Alternatively, the values may be obtained by testing random blood samples. The distances r1, r2, and r3 are determined based on the respective impedance using a transfer function or any other mathematical technique in conjunction with the look-up table. Because the relative positions of the electrodes 205 on the reference catheter 128 and the electrodes 201 on the catheter 124 are known, the distances d1 and d2 as well as the angles $\alpha 1$, $\alpha 2$, $\alpha 3$, $\beta 1$, $\beta 2$, and $\beta 3$ can be determined. The relative distances and angles may be used in triangulation formulas, trigonometric equations, and/or any other known or future mathematical techniques to derive a three point coordinate position of the electrode 201. Ultimately, the position of the catheter 124 is determined because the placement of the electrodes 201 on the catheter 124 is known. Positions may be determined for any number of electrodes 201 as well as any number of different catheters.

Alternatively, instead of calculating blood impedance, a voltage potential between a certain electrode 205 and a certain electrode 201 may be measured to determine the distance between the electrodes. For example, when one electrode 205 is transmitting or receiving a signal from one electrode 201, an electric field is generated due to the current flow. Therefore, a voltage potential, created by the electric field, may be measured between another electrode 205, such as an electrode adjacent to the transmitting or receiving electrode 205, and another electrode 201, such as an electrode adjacent to the transmitting or receiving electrode 201. The different voltage potentials between electrodes relate to the distances between the same electrodes. For example, the voltage measured will increase as the distance between electrodes increases. A predetermined look-up table may be used to store distance values that correlate to different voltage potentials. These values may be obtained by testing the patient 112 or other patients. Alternatively, the values may be obtained by testing random blood samples. The distances r1, r2, and r3 are determined based on the respective voltage potential using a transfer function or any other mathematical technique in conjunction with the look-up table. The distances d1 and d2 as well as the angles $\alpha 1$, $\alpha 2$, $\alpha 3$, $\beta 1$, $\beta 2$, and $\beta 3$ can be determined by any technique described above.

The electrodes 201 and 205 are unlike magnetic coils that create an electromagnetic field to induce electric currents in adjacent coils. The amplitude of the electric current is proportional to the distance from the coil generating the field. Hence, the amplitude of the induced current is a measure of the distance. The angle of the coil in relation to the magnetic field is also of importance. When three perpendicular coils are positioned at the tip of a catheter, three electrical currents can be measured in which the geometric relation also gives information of catheter direction. However, using electrodes does not involve generating electromagnetic fields to induce electric currents in adjacent coils. An electric current is sent from one electrode to another to create a potential field through the blood pool and/or tissue between the electrodes where a continuous potential drop is created. The electric current is generated using phase shifting as described above. For example, the current is about 0.1 mA at 10 kHz. In this way, impedance and/or voltage potential relating to distance may be determined. Also, the electric current is continuously moving or changing as the catheter 124 is moving.

Also, the magnetic coil approach includes coils generating the field that need to be positioned at a known position either inside or outside the patient 112 as well as measurement coils that need to be integrated in the catheter. Therefore, specific catheters are used, unlike the electrode approach in which catheters with simple electrodes may be used. The position is determined without using electrodes external to the patient, but such electrodes may be used.

Figure 3:
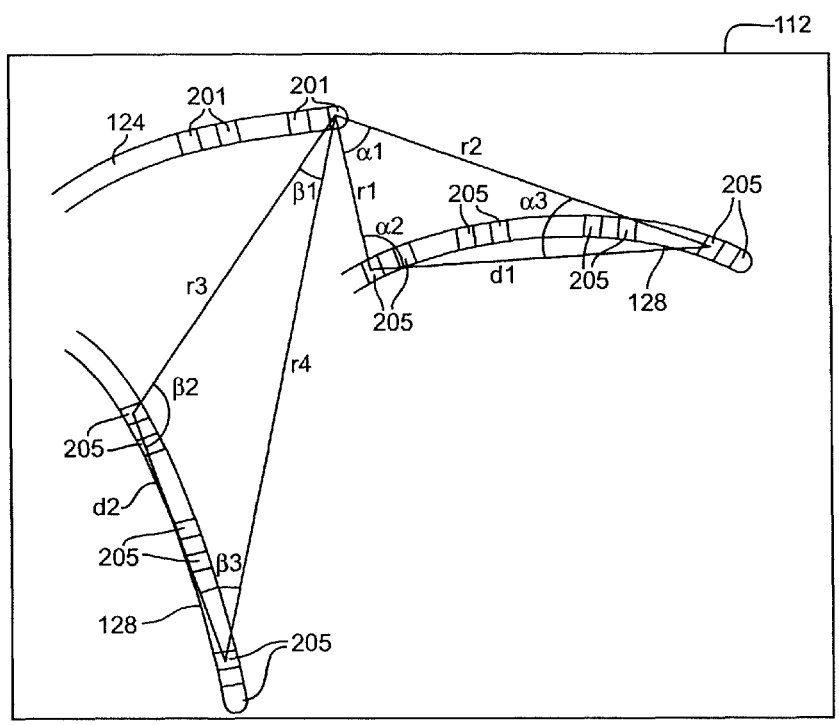
FIG. 3 is a magnified view of a first alternate embodiment of the system for determining a position of a catheter of FIG. 1.

FIG. 3 is a magnified view of a first alternate embodiment of the system for determining a position of the catheter 124. In this embodiment, two reference catheters 128 are used. However, any number of reference catheters 128 may be used. More reference catheters 128 allow for more accurate position data. The reference catheters 128 can be positioned in any direction in the patient 112. For example, the reference catheters 128 are positioned at an angle to each other. Therefore, the reference catheters 128 may be substantially straight. Alternatively, the reference catheters 128 are curvilinear in shape.

The reference catheters 128 share the same voltage or current generator or they each utilize a separate generator. As mentioned above, a position of the catheter 124 is determined based the signals transmitted and received between the electrodes 201 and 205, respectively. Relative distances between the electrodes 201 and 205 are determined by blood impedance, voltage potential, and/or any other electrical characteristic. The distances r1, r2, r3, r4, d1 and d2 as well as the angles .alpha.1, .alpha.2, .alpha.3, .beta.1, .beta.2, and .beta.3 can be determined by any technique described above.

Figure 4:
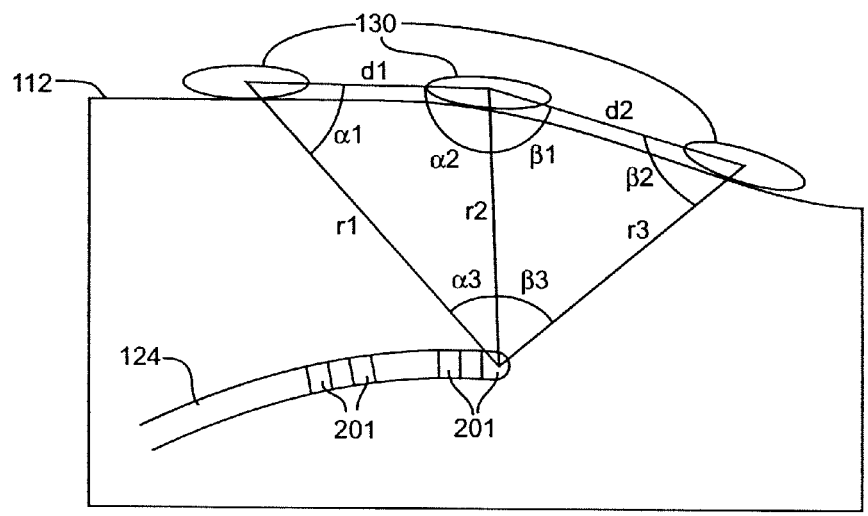
FIG. 4 is a magnified view of a second alternate embodiment of the system for determining a position of a catheter of FIG. 1.
Figure 5:
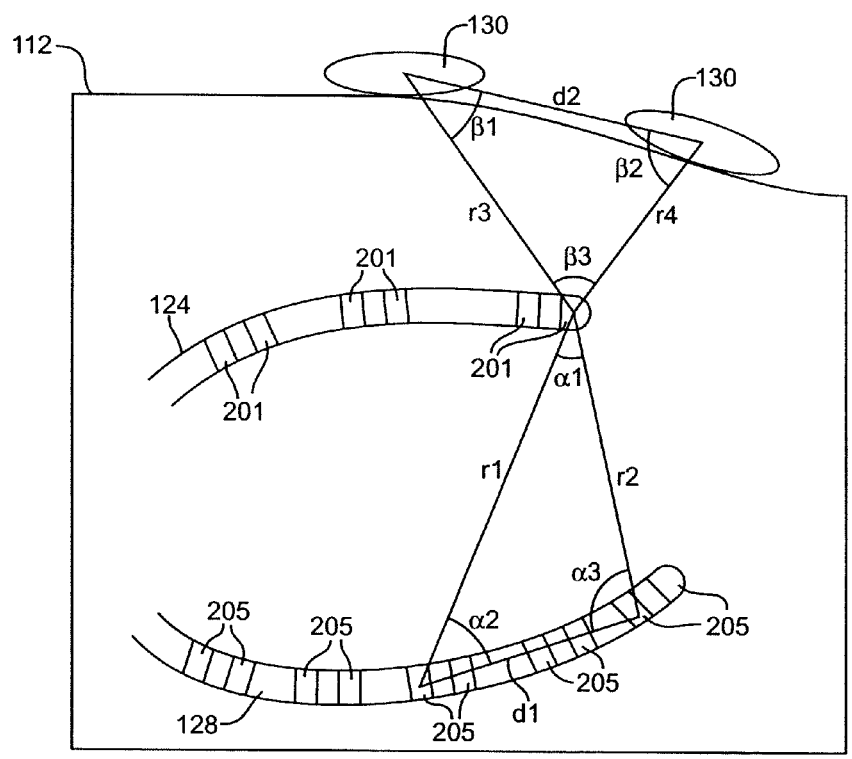
FIG. 5 is a magnified view of a third alternate embodiment of the system for determining a position of a catheter of FIG. 1.

FIG. 4 is a magnified view of a second alternate embodiment of the system for determining a position of the catheter 124. In this case, the body surface electrodes 130 are used as reference electrodes instead of the reference catheter 128. The body surface electrodes 130 are placed on any part of the patient 112's body. For example, the body surface electrodes 130 are not positioned on or in the body surface along three mutually orthogonal axes. Instead, the electrodes 130 may be positioned based on body location or more random locations on the patient. The body surface electrodes 130 are made of any metal material or any known or future material operable to transmit and receive electrical signals. For example, the body surface electrodes 130 are electrocardiogram ("ECG") electrodes. Alternatively, the body surface electrodes 130 are made of a non-magnetic material that may be scanned with a magnetic resonance imaging ("MRI") system and yet still transmit and receive electrical signals. For example, titanium or carbon fiber material may be used. Also, the body surface electrodes 130 may be needle or pin electrodes that can be inserted in the body surface of the patient 112. The body surface electrodes 130 are connected with the electrode system 120 or a separate or included ECG system. The electrodes 201 are also connected with a voltage or current generator, which may or may not be part of the electrode system 120 or the ECG system. The generator is connected with all or some of the electrodes 130.

The operation of the body surface electrodes 130 and the electrodes 201 configuration is substantially similar to the reference catheter 128 and the catheter 124 configuration, as described above. The position of the electrode 201 is determined based on the signals transmitted and received between the electrodes 201 and 130, respectively. Relative distances between the electrodes 201 and 130 are determined by impedance, voltage potential, and/or any other electrical characteristic. In this case, in addition to blood impedance, an impedance of other tissue, such as lung tissue as well as other thoracic impedance, is determined. A predetermined look-up table may be used to store distance values that correlate to combinations of different impedances. These values may be obtained by testing the patient 112 or other patients. Alternatively, the values may be obtained by testing random blood and other tissue samples. The distances r1, r2, r3, d1 and d2 as well as the angles α1, α2, α3, β1, β2, and β3 can be determined by any technique described above.

The impedance between the catheter electrodes and the body surface electrodes may vary due to motion when the patient 112 is breathing, inflation of air in the lungs, and possibly varying contact impedance of each of the body surface electrodes. To compensate for this, breathing activity may be measured and used in a feed forward compensation. Alternatively, filters to remove the low frequency disturbing variation may be utilized.

Any number and combinations of the body surface electrodes 130 and the reference catheters 128 may be utilized to determine the position of the catheter 124. For example, referring to FIG. 5, one reference catheter 128 is used in conjunction with two body surface electrodes 130 to determine the position of the catheter 124. However, any number of reference catheters 128 and body surface electrodes 130 may be used. For example, at least two reference catheters 128 and at least six body surface electrodes 130 are utilized. More reference catheters 128 and body surface electrodes 130 that are used allow for more accurate position data.

The reference catheter 128 and the body surface electrodes 130 share the same voltage or current generator or they each utilize a separate generator. As mentioned above, a position of the catheter 124 is determined based on the signals transmitted and received between the electrodes 201, 205, and 130, respectively. Relative distances between the electrodes 201, 205, and 130 are determined by impedance, such as thoracic and blood impedance, voltage potential, and/or any other electrical characteristic. The distances r1, r2, r3, r4, d1 and d2 as well as the angles α1, α2, α3, β1, β2, and β3 can be determined by any technique described above.

Figure 6:
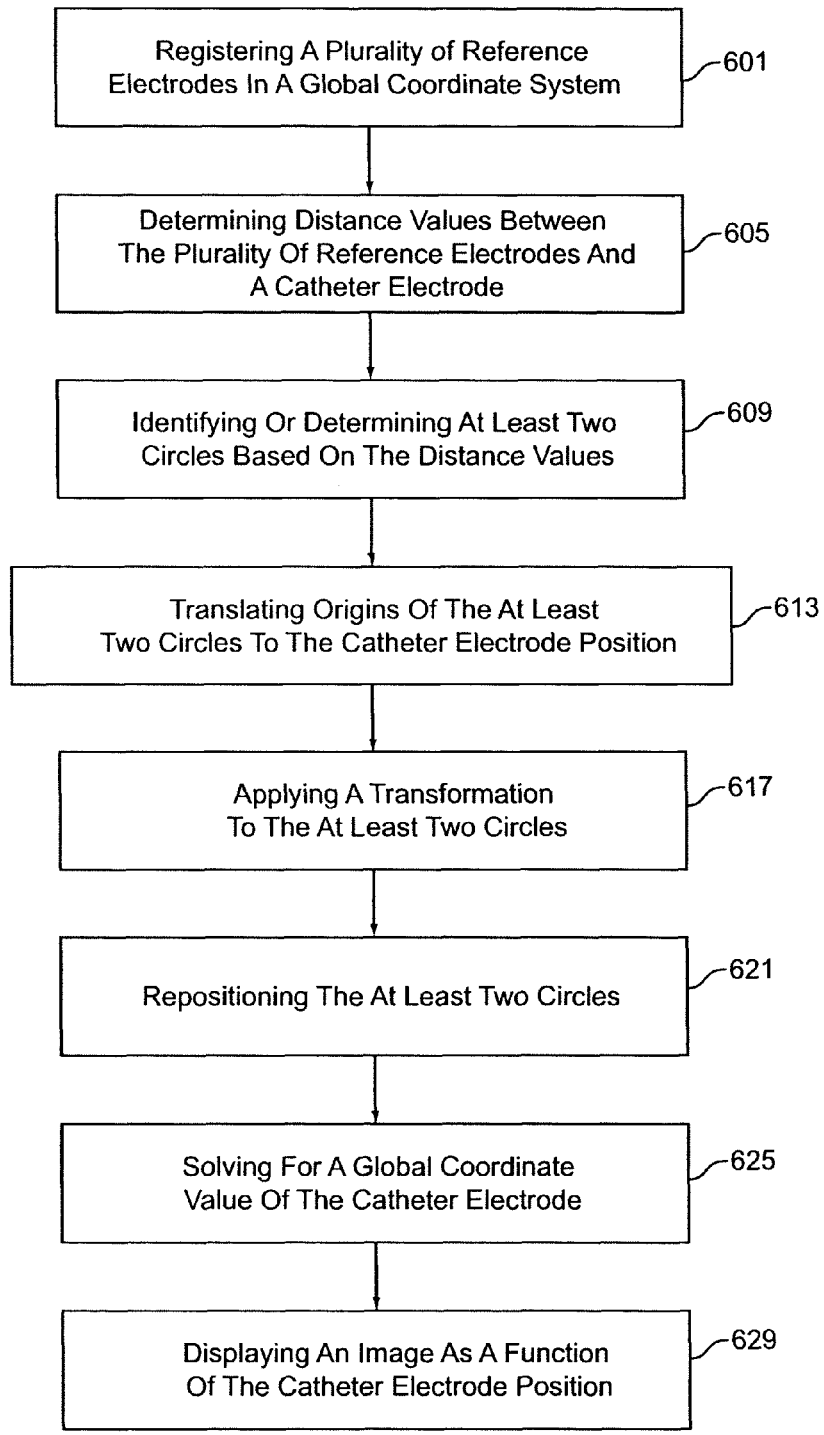
FIG. 6 is a flowchart illustrating one embodiment of a method for localizing a catheter.

As an alternative to the techniques described above to determine a position of the electrode 201, localization of the catheter 124 may be accomplished using transformation. FIG. 6 is a flowchart illustrating one embodiment of a method for localizing a catheter. Fewer or more acts may be provided. A processor, such as the processor 102 or 130, is operable to implement the following acts in the order shown or a different order.

In act 601, a plurality of reference electrodes, such as the electrodes 205 and 130, are registered in a global 3D coordinate system. The global 3D coordinate system represents positions of image objects in relation to three perpendicular axes. For example, 3D coordinate values are designated to the reference electrodes during calibration (calibration is described below). X-ray image segmentation or any other imaging technique is used to determine the position of the reference electrodes. Alternatively, 3D coordinate values are designated to the reference electrodes before or after calibration.

Figure 7:
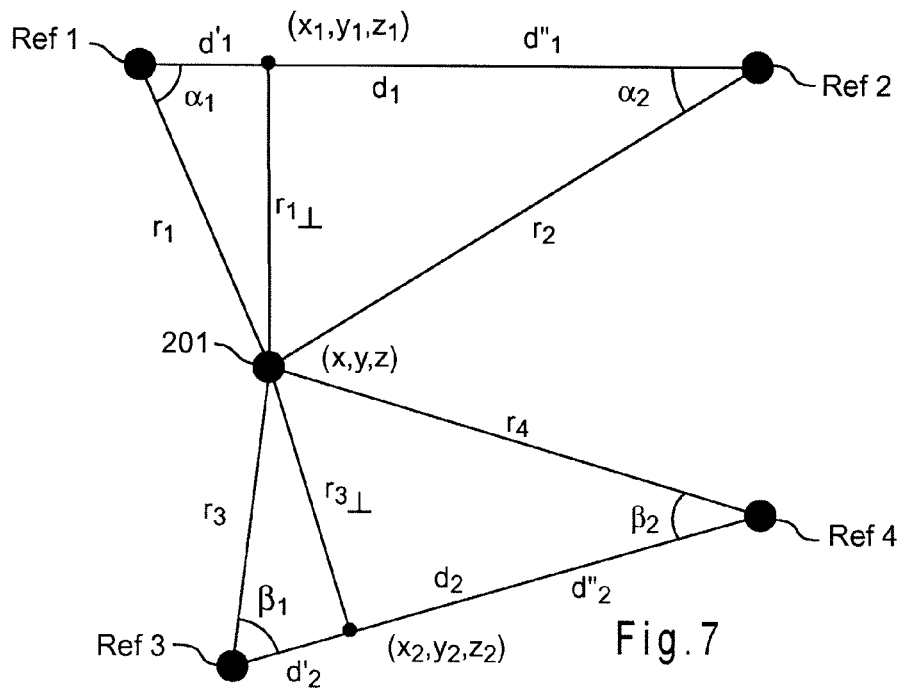
FIG. 7 is a geometric diagram illustrating one embodiment of localizing a catheter.

In act 605, distance values between the plurality of reference electrodes and a catheter electrode, such as the electrode 201, are determined. FIG. 7 represents geometric dimensions between reference electrodes and the catheter electrode 201. At least four reference electrodes, ref 1, ref 2, ref 3, and ref 4, have known 3D coordinate values (based on registration) and form at least two triangles in relation to the catheter electrode 201. Alternatively, three reference electrodes may be used in which the two triangles share a side. For example, the reference electrodes ref 2 and ref 4 are the same point. The distance, $d_1$, between the reference electrodes ref 1 and ref 2 and the distance, $d_2$, between the reference electrodes ref 3 and ref 4 are determined by the equations (1) and (2):

$$d_1 = \sqrt{(x_{ref1} - x_{ref2})^2 + (y_{ref1} - y_{ref2})^2 + (z_{ref1} - z_{ref2})^2} \quad (1)$$

$$d_2 = \sqrt{(x_{ref3} - x_{ref4})^2 + (y_{ref3} - y_{ref4})^2 + (z_{ref3} - z_{ref4})^2} \quad (2)$$

The distances, $r_1$, $r_2$, $r_3$, and $r_4$, between the reference electrodes and the catheter electrode 201 are estimated or determined by the impedance and/or voltage potential calculations described above. Because the distance values $d_1$, $d_2$, $r_1$, $r_2$, $r_3$, and $r_4$ are known, the relative triangle angles, $\alpha_1$, $\alpha_2$, $\beta_1$, and $\beta_2$ are determined using equations (3), (4), (5), and (6) respectively:

$$r_2^2 = r_1^2 + d_1^2 - 2 \cdot r_1 \cdot d_1 \cdot \cos(\alpha_1) \quad (3)$$

The angle $\alpha_1$ from (3) can be expressed as $$\alpha_1 = a\cos\left(\frac{r_1^2 + d_1^2 - r_2^2}{2 \cdot r_1 \cdot d_1}\right) \quad (4)$$

$$r_1 \cdot \sin(\alpha_2) = r_2 \cdot \sin(\alpha_1)$$

the angle $\alpha_2$ from (4) can be expressed as $$\alpha_2 = a\sin\left(\frac{r_2}{r_1} \cdot \sin(\alpha_1)\right)$$

A similar sequence of calculations is used to represent $\beta_1$ and $\beta_2$ as $$\beta_1 = a\cos\left(\frac{r_3^2 + d_2^2 - r_4^2}{2 \cdot r_3 \cdot d_2}\right) \quad (5)$$

$$\beta_2 = a\sin\left(\frac{r_4}{r_3} \cdot \sin(\beta_1)\right) \quad (6)$$

After the angles, $\alpha_1$, $\alpha_2$, $\beta_1$, and $\beta_2$ are determined, the shortest distance, $r_{1orthogonal}$, from the distance $d_1$ to the catheter electrode 201 and the shortest distance, $r_{3orthogonal}$, from the distance $d_2$ to the catheter electrode 201 are determined using the equations (7) and (8), respectively:

$$r_{1\perp} = r_1 \cdot \sin(\alpha_1) = r_2 \cdot \sin(\alpha_2) \quad (7)$$

$$r_{3\perp} = r_3 \cdot \sin(\beta_1) = r_4 \cdot \sin(\beta_2) \quad (8)$$

The distances from each reference electrode, $d'_1$, $d''_1$, $d'_2$, and $d''_2$, to the position of $r_{1orthogonal}$ and $r_{3orthogonal}$, respectively, are determined by the equations (9), (10), (11), and (12), respectively, as:

$$d'_1 = \begin{cases} r_1 \cdot \cos(\alpha_1) & \text{if } \alpha_1 \in \left[0, \frac{\pi}{2}\right] \text{rad} \\ -r_1 \cdot \cos(\alpha_1) & \text{if } \alpha_1 \in \left[\frac{\pi}{2}, 0\right] \text{rad} \end{cases} \quad (9)$$

$$d''_1 = \begin{cases} r_2 \cdot \cos(\alpha_2) & \text{if } \alpha_2 \in \left[0, \frac{\pi}{2}\right] \text{rad} \\ -r_2 \cdot \cos(\alpha_2) & \text{if } \alpha_2 \in \left[\frac{\pi}{2}, \pi\right] \text{rad} \end{cases} \quad (10)$$

$$d'_2 = \begin{cases} r_3 \cdot \cos(\beta_1) & \text{if } \beta_1 \in \left[0, \frac{\pi}{2}\right] \text{rad} \\ -r_3 \cdot \cos(\beta_1) & \text{if } \beta_1 \in \left[\frac{\pi}{2}, \pi\right] \text{rad} \end{cases} \quad (11)$$

$$d''_2 = \begin{cases} r_4 \cdot \cos(\beta_2) & \text{if } \beta_2 \in \left[0, \frac{\pi}{2}\right] \text{rad} \\ -r_4 \cdot \cos(\beta_2) & \text{if } \beta_2 \in \left[\frac{\pi}{2}, \pi\right] \text{rad} \end{cases} \quad (12)$$

Based on the $d'_1$, $d''_1$, $d'_2$, and $d''_2$ values, a 3D coordinate point, $(x_1, y_1, z_1)$, where $r_{1orthogonal}$ crosses the distance $d_1$ and a 3D coordinate point, $(x_2, y_2, z_2)$, where $r_{3orthogonal}$ crosses the distance $d_2$, are determined by the equations (13) or (14) and (15) or (16), respectively:

$$x_1 = x_{ref1} + \frac{d'_1}{d_1} \cdot (x_{ref1} - x_{ref2}) \quad (13)$$

$$y_1 = y_{ref1} + \frac{d'_1}{d_1} \cdot (y_{ref1} - y_{ref2})$$

$$z_1 = z_{ref1} + \frac{d'_1}{d_1} \cdot (z_{ref1} - z_{ref2})$$

$$x_1 = x_{ref2} + \frac{d''_1}{d_1} \cdot (x_{ref2} - x_{ref1}) \quad (14)$$

$$y_1 = y_{ref2} + \frac{d''_1}{d_1} \cdot (y_{ref2} - y_{ref1})$$

$$z_1 = z_{ref2} + \frac{d''_1}{d_1} \cdot (z_{ref2} - z_{ref1})$$

$$x_2 = x_{ref3} + \frac{d'_2}{d_2} \cdot (x_{ref3} - x_{ref4}) \quad (15)$$

$$y_2 = y_{ref3} + \frac{d'_2}{d_2} \cdot (y_{ref3} - y_{ref4})$$

$$z_2 = z_{ref3} + \frac{d'_2}{d_2} \cdot (z_{ref3} - z_{ref4})$$

$$x_2 = x_{ref4} + \frac{d''_2}{d_2} \cdot (x_{ref4} - x_{ref3}) \quad (16)$$

$$y_2 = y_{ref4} + \frac{d''_2}{d_2} \cdot (y_{ref4} - y_{ref3})$$

$$z_2 = z_{ref4} + \frac{d''_2}{d_2} \cdot (z_{ref4} - z_{ref3})$$

The distances from the $(x_1, y_1, z_1)$ point to the catheter electrode point $(x, y, z)$ and the $(x_2, y_2, z_2)$ point to the catheter point $(x, y, z)$ are known, but the angles of the vectors $r_{1orthogonal}$ and $r_{3orthogonal}$ in relation to the catheter point $(x, y, z)$ are not determined. In act 609, at least two circles based on the determined distance values are identified or determined. For example, the point $(x_1, y_1, z_1)$ is designated as the origin of one of the at least two circles with a radius being the vector $r_{1orthogonal}$, and the point $(x_2, y_2, z_2)$ is designated as the origin of the other one of the at least two circles with a radius being the vector $r_{3orthogonal}$. Therefore, the catheter point $(x, y, z)$ is located at a place where the at least two circles substantially coincide. However, the circles might not coincide due to measurement errors caused by noise and/or motion, and, so, the point $(x, y, z)$ may be located within a minimum distance between the at least two circles.

To simplify the calculations of the at least two circles, a local coordinate system for each of the at least two circles is established. For example, the z-axis for one of the circles is fixed to the direction of $d_1$, and the z-axis for the other circle is fixed to the direction of $d_2$. The points $(x_1, y_1, z_1)$ and $(x_2, y_2, z_2)$ are designated as the origins of the two local coordinate systems, respectively.

In act 613, the origins of the at least two circles are translated to the catheter electrode point $(x, y, z)$. The point $(x, y, z)$ is designated as the origin of the global 3D coordinate system. The translation is a linear translation that may include addition or multiplication calculations. Alternatively, any other translation other than a linear translation may be used. By placing the at least two circles in the origin of the global 3D coordinate system, the local coordinates of the circle can be expressed in the global 3D coordinate system by applying a transformation.

Figure 8:
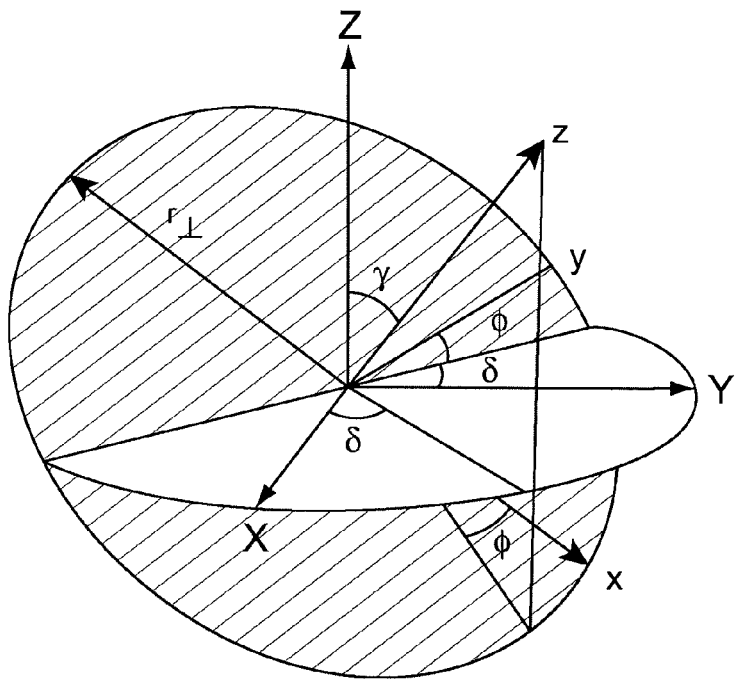
FIG. 8 is a diagram illustrating transformation features.

In act 617, a transformation is applied to the at least two circles. For example, an Euler transformation is utilized. Alternatively, any transformation to express an object in a general coordinate system may be used. FIG. 8 is a diagram illustrating transformation features in which the X, Y, and Z axes represent the global 3D coordinate system. For the Euler transformation, rotation matrices are determined. The range of the Euler angles $\delta$, $\gamma$, and $\phi$ given in radians are:

$$0 \le \delta \le 2 \cdot \pi$$

$$0 \le \gamma \le \pi$$

$$0 \le \phi \le 2 \cdot \pi$$

A first rotation matrix is determined when a circle is rotated about the Z-axis as in equation (17):

$$R_z(\delta) = \begin{bmatrix} \cos(\delta) & \sin(\delta) & 0 \\ -\sin(\delta) & \cos(\delta) & 0 \\ 0 & 0 & 1 \end{bmatrix} \quad (17)$$

The Euler angle $\delta$, which represents a phase shift and is a constant angle in the X-Y plane, is derived as in equation (18):

$$\delta = \pi - a\tan\left(\frac{dy}{dx}\right), \quad (18)$$

$$d_y = y_{ref(i+1)} - y_{ref(i)},$$

$$d_x = x_{ref(i+1)} - x_{ref(i)}$$

A second rotation matrix is determined when the local z-axis is turned or flipped from the Z-axis as in equation (19):

$$R_y(\gamma) = \begin{bmatrix} \cos(\gamma) & 0 & -\sin(\gamma) \\ 0 & 1 & 0 \\ \sin(\gamma) & 0 & \cos(\gamma) \end{bmatrix} \quad (19)$$

The Euler angle $\gamma$, which represents a constant tilt angle from the Z-axis, is derived as in equation (20):

$$\gamma = a\cos\left(\frac{dz}{d}\right) \quad (20)$$

A third rotation matrix is determined when a flipped circle is rotated about the z-axis as in equation (21):

$$R_z(\phi) = \begin{bmatrix} r_\perp \cdot \cos(\phi) \\ r_\perp \cdot \sin(\phi) \\ 0 \end{bmatrix} \quad (21)$$

The angle $\phi$ is a rotation angle ranging from 0 to $2\pi$ radians.

For the transformation, the matrices are multiplied together to obtain an expression of the global 3D coordinates of each of the at least two circles as in equation (22):

$$R_z(\delta) \cdot R_y(\gamma) \cdot R_z(\phi) \quad (22)$$

The multiplication of the matrices allow for mathematical derivation of the catheter electrode point (x, y, z). Because the $\delta$ and $\gamma$ values are determined for each circle, the (x, y, z) point can be calculated when the angles $\phi$ for where the at least two circles coincide are determined.

For example, the first and second rotation matrices for one of the at least two circles are expressed in equations (23) and (24):

$$R_z(\delta_1) = \begin{bmatrix} \cos(\delta) & \sin(\delta) & 0 \\ -\sin(\delta_1) & \cos(\delta_1) & 0 \\ 0 & 0 & 1 \end{bmatrix} = \begin{bmatrix} a_{11} & a_{12} & 0 \\ a_{21} & a_{22} & 0 \\ 0 & 0 & 1 \end{bmatrix} \quad (23)$$

$$R_z(\gamma_1) = \begin{bmatrix} \cos(\gamma_1) & 0 & -\sin(\gamma_1) \\ 0 & 1 & 0 \\ \sin(\gamma_1) & 0 & \cos(\gamma_1) \end{bmatrix} = \begin{bmatrix} b_{11} & 0 & b_{13} \\ 0 & 1 & 0 \\ b_{31} & 0 & b_{33} \end{bmatrix} \quad (24)$$

The first and second rotation matrices for the other one of the at least two circles are expressed in equations (25) and (26):

$$R_z(\delta_2) = \begin{bmatrix} \cos(\delta_2) & \sin(\delta_2) & 0 \\ -\sin(\delta_2) & \cos(\delta_2) & 0 \\ 0 & 0 & 1 \end{bmatrix} = \begin{bmatrix} a'_{11} & a'_{12} & 0 \\ a'_{21} & a'_{22} & 0 \\ 0 & 0 & 1 \end{bmatrix} \quad (25)$$

$$R_y(\gamma_2) = \begin{bmatrix} \cos(\gamma_2) & 0 & -\sin(\gamma_2) \\ 0 & 1 & 0 \\ \sin(\gamma_2) & 0 & \cos(\gamma_2) \end{bmatrix} = \begin{bmatrix} b'_{11} & 0 & b'_{13} \\ 0 & 1 & 0 \\ b'_{31} & 0 & b'_{33} \end{bmatrix} \quad (26)$$

The multiplication of the matrices renders equations of the at least two circles in the global 3D coordinate system as in equations (27) and (28):

$$x_{1\_circ} = a_{11} \cdot b_{11} \cdot r_{1\perp} \cdot \cos(\phi_1) + a_{12} \cdot r_{1\perp} \cdot \sin(\phi_1)$$

$$y_{1\_circ} = a_{21} \cdot b_{11} \cdot r_{1\perp} \cdot \cos(\phi_1) + a_{22} \cdot r_{1\perp} \cdot \sin(\phi_1)$$

$$z_{1\_circ} = b_{31} \cdot r_{1\perp} \cdot \cos(\phi_1) \quad (27)$$

$$y_{2\_circ} = a_{11}' \cdot b_{11}' \cdot r_{2\perp} \cdot \cos(\phi_2) + a_{12}' \cdot r_{2\perp} \cdot \sin(\phi_2)$$

$$y_{2\_circ} = a_{21}' \cdot b_{11}' \cdot r_{2\perp} \cdot \cos(\phi_2) + a_{22}' \cdot r_{2\perp} \cdot \sin(\phi_2)$$

$$z_{2\_circ} = b_{31}' \cdot r_{2\perp} \cdot \cos(\phi_2) \quad (28)$$

In act 621, the at least two circles are repositioned from the origin of the global coordinate system to their original position coordinates. For example, an inverse linear translation is used. Alternatively, any other mathematical translation may be used to position the origins of the at least two circles to the $(x_1, y_1, z_1)$ and $(x_2, y_2, z_2)$ points. The at least two circles with the origins at the $(x_1, y_1, z_1)$ and $(x_2, y_2, z_2)$ points expressed in the global 3D coordinate system are represented by equations (30) and (31):

$$\text{circle\_1} = (x_1 + x_{1\_circ})\hat{X} + (y_1 + y_{1\_circ})\hat{Y} + (z_1 + z_{1\_circ})\hat{Z} \quad (30)$$

$$\text{circle\_2} = (x_2 + x_{2\_circ})\hat{X} + (y_2 + y_{2\_circ})\hat{Y} + (z_2 + z_{2\_circ})\hat{Z} \quad (31)$$

In act 625, a global 3D coordinate value of the catheter electrode 201 is solved for using the equation (32):

$$|\text{circle\_1} - \text{circle\_2}|^2 = (x_1 - x_2 + x_{1\_circ} - x_{2\_circ})^2 + (y_1 - y_2 + y_{1\_circ} - y_{2\_circ})^2 + (z_1 - z_2 + z_{1\_circ} - z_{2\_circ})^2 \quad (32)$$

The position of the catheter electrode 201, (x, y, z), is located where the at least two circles substantially coincide or within a minimum distance between the at least two circles. Therefore, the equation (32) is set to zero and the circle values are mathematically determined. Alternatively, a minimum distance is numerically found by letting the angles $\phi_1$ and $\phi_2$ run from 0 to $2\pi$ in the equations (27) and (28) and determining the angles $\phi_1$ and $\phi_2$ that produce the minimum distance in equation (32). Once the angles $\phi_1$ and $\phi_2$ are determined, the circular values for the at least two circles can be determined using the equations (27) and (28). The catheter electrode point (x, y, z) in the global 3D coordinate system is determined using the equations (30) and (31). The equations (30) and (31) should produce the same point where the at least two circles coincide. However, due to noise and/or calculation error, two points may be calculated with a gap between them. An average of the two points is mathematically calculated to determine an average position of the catheter electrode 201. The position or location of any number of the catheter electrodes 201 may be determined using the techniques and calculations described above.

In act 629, an image as a function of the catheter electrode 201 position is displayed. For example, the global 3D coordinate position data is used in conjunction with volume data or other image data of the patient 112 to create a 3D or virtual image of the catheter 124 during or after the medical procedure, as described below.

In any of the embodiments described above, more accurate position data is obtained, especially for non-homogenous blood and other tissue characteristics between different patients 112 or in the same patient 112, by calibrating the catheter 124 with the reference catheters 128 and/or the body surface electrodes 130. Calibration involves generating images, such as X-ray image segmentations, while transmitting and receiving electrical signals between the electrodes 205, 130, and 201. The X-ray images are taken when the catheter 124 is positioned in different locations and the reference catheters 128 and/or the body surface electrodes 130 remain in the same position. A correlation between the actual distances between electrodes determined by the images and the distances estimated by the electrode system 120 may be obtained. The correlations are stored in the memory 140 and/or 106 and are relied on to obtain accurate position data of the catheter 124 during medical procedures. The correlations may be used in conjunction with the predetermined look up tables, described above, to adjust the distance values appropriately. For example, an adjusted offset based on a correlation is added to an output of a predetermined look up table.

Heart beat and breathing patterns can be compensated for by using a variety of techniques. For example, position data may be determined once during every heart beat or breathing cycle by triggering the electrode system 120 with the respective physiological cycle. Any other known or future physiological compensation technique may be utilized.

Figure 9:
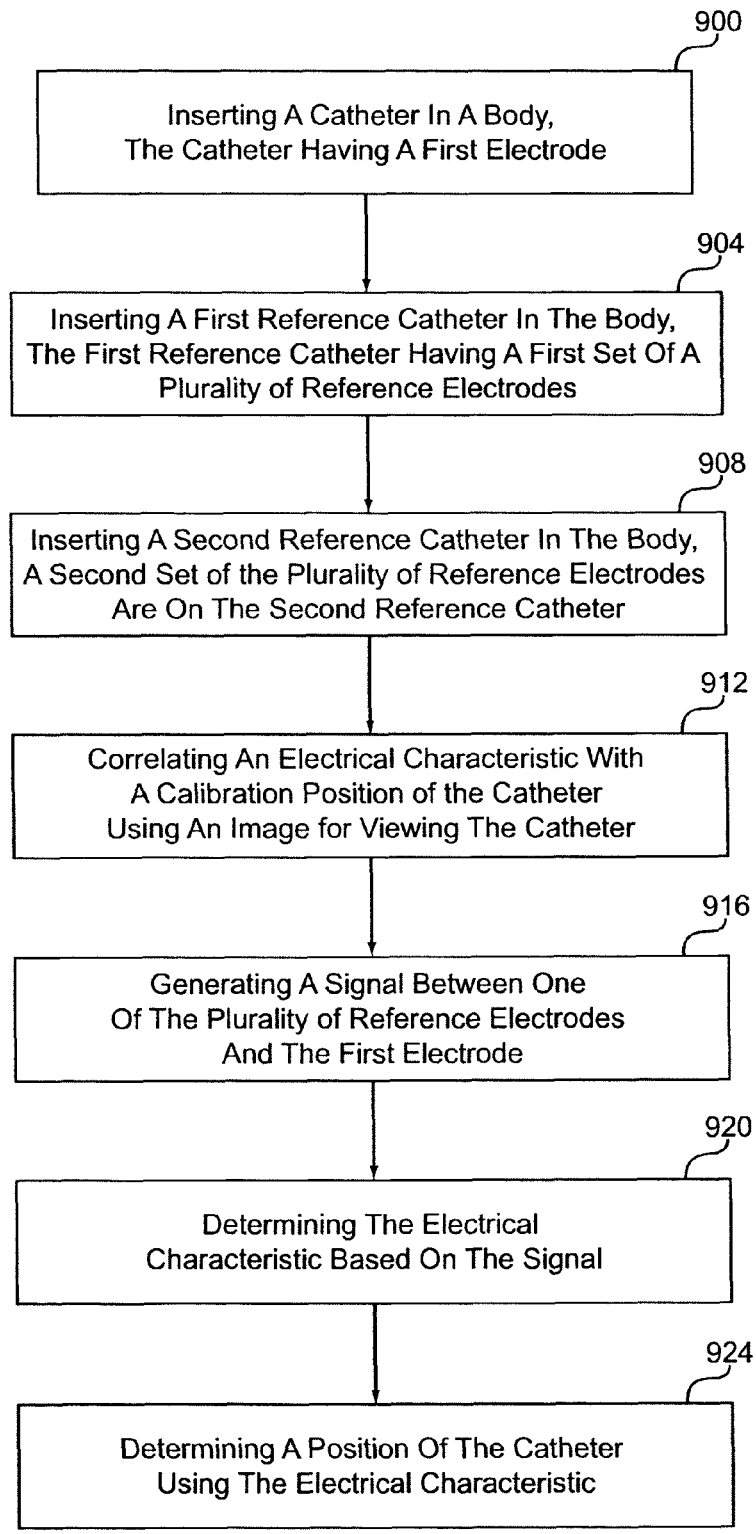
FIG. 9 is a flowchart illustrating one embodiment of a method for determining a position of a catheter.

FIG. 9 is a flowchart illustrating one embodiment of a method for determining a position of the catheter 124. In act 900, a catheter is inserted in a body, such as the body of the patient 112. The catheter is any treatment or measurement catheter, such as the catheter 124, including electrodes on the body of the catheter. Any known or future methods of inserting the catheter may be utilized. For example, an incision is made in the patient 112, such as in the arm or the leg, and the catheter 124 is inserted into the incision by a doctor, medical professional, and/or machine. Alternatively, a needle or puncturing device may be inserted into the patient 112, and the catheter 124 follows the puncturing device. Or, the catheter 124 is inserted into any orifice or opening of the patient 112. Any known or future lubricant or mechanical, electrical, and/or catheter guide may be used in assisting with inserting the catheter 124 into the patient 112.

In act 904, a first reference catheter is inserted in the body. The first reference catheter is any catheter including a first set of a plurality of reference electrodes, such as the reference catheter 128. Any of the methods of inserting a catheter in a body described above may be utilized to insert the first reference catheter. Alternatively, body surface electrodes, such as the electrodes 130, are attached on the body surface of the patient 130 instead of inserting the first reference catheter. For example, the electrodes 130 are not positioned on or in the body surface of the patient 112 along three mutually orthogonal axes.

In act 908, a second reference catheter is inserted in the body. The second reference catheter is any catheter including a second set of the plurality of reference electrodes, such as another reference catheter 128. Any of the methods of inserting a catheter in a body described above may be utilized to insert the second reference catheter. Alternatively, body surface electrodes, such as the electrodes 130, are attached on the body surface of the patient 130 instead of inserting the second reference catheter. For example, the electrodes 130 are not positioned on or in the body surface of the patient 112 along three mutually orthogonal axes.

In act 912, a calibration procedure is performed. For example, once the first reference catheter, the second reference catheter, and/or the body surface electrodes are positioned in or on the patient 112, they remain at their respective positions. The catheter 124 is then moved to one region within the body, and the electrodes 201 and the electrodes 205 and/or 130 transmit and receive electrical signals between each other, respectively.

Voltage or current generators connected with the electrodes generate a current between two specific electrodes. For example, a generator is connected with the electrodes 201 and one or more generators are connected with the reference electrodes 205 and/or 130. The generators may be connected with all or some of the respective electrodes. The generators are phase shifted 180 degrees to allow for a path of least resistance between any two electrodes. The electrical signals between the electrodes may be AC or DC signals. When using AC signals, sequential transmission of the signals between electrodes is performed to allow for the use of a substantially same frequency. Alternatively, more generators may be used to transmit and receive electrical signals between electrodes at different frequencies.

While electrical signals are being generated between the electrodes when the catheter 124 is in the first position, images, such as X-ray images, are taken. The actual distances between the electrodes 201 and the reference electrodes 205 and/or 130 are determined from the images, and the distances are correlated with estimated distance values. The estimated distance values directly relate to impedance values or voltage potential values determined based on the electrical signals. For example, a medical professional obtains actual distance data from the images and compares the actual distance data with the estimated distance data determined by the electrode system 120. Compensation values based on the comparison are manually entered into the electrode system 120 for calibration purposes. Alternatively, the imaging system 100 determines the actual distance values based on the images, and the actual distance data is transmitted or transferred to the electrode system 120. Then the electrode system 120 calculates the respective compensation factors for calibration.

The catheter 124 is then moved to a second position. Electrical signals are transmitted between the electrodes 201 and 205 and/or 130 while images are taken for the new position. The same methods of calibration are performed for the second position as was performed for the first position. More positions the catheter 124 allow for a better calibration. Physical differences between different patients 112 or within the same patient 112 may be compensated.

After calibration, capturing images during medical procedures using the catheter 124 may not be needed. For example, X-ray exposure to the patient 112 is minimized. Also, during treatment or measurement medical procedures, the catheter 124 is moved to a variety of positions by a medical professional, and the reference catheters 128 and/or body surface electrodes 130 remain substantially at the same position. The position of the catheter 124 during the procedures is determined.

For example, in act 916, an electrical signal is generated between at least one of the plurality of reference electrodes 205 and/or 130 and at least one electrode 201. The generation and characteristic of the signal is described above.

In act 920, an electrical characteristic is determined based on the signal. The electrical characteristic is a blood impedance, any other tissue impedance, such as impedance of lung tissue as well as other thoracic impedances, a voltage potential, and or any other electrical characteristic.

For example, when a current is flowing between one of the electrodes 201 and one of the electrodes 205 or 130, an impedance can be calculated based on the voltage applied and the actual current value. This impedance is different for different distances between electrodes, and therefore, the impedance is used to estimate distances between electrodes.

Alternatively, instead of using impedances, voltage potentials between electrodes may be used. For example, when a current is flowing between one of the electrodes 201 and one of the electrodes 205 or 130, an electric field is generated in the same direction as the current. Then a voltage potential, based on the electric field, is measured between two non-transmitting and/or non-receiving electrodes, such as between an electrode 201 adjacent to the transmitting and/or receiving electrode 201 and an electrode 205 or 130 adjacent to the transmitting and/or receiving electrode 205 or 130. The voltage potential is different for different distances between electrodes, and, therefore, the voltage potential is used to estimate distances between electrodes.

In act 924, a position of the catheter 124 is determined based on the electrical characteristic. For example, estimated distances are determined based on the impedance or voltage potential values using a transfer function or any other mathematical technique. Because the position of the reference electrodes 205 and/or 130 are known, the position of the electrodes 201 are determined based on the estimated distances using standard triangulation formulas, trigonometric equations, and/or any other known or future mathematical techniques to derive a three point coordinate position of the electrode 201. Alternatively, the transformation method described above may be utilized. The correlated calibration values are used to adjust the estimated distances to obtain more accurate position data. Because the positions of the electrodes 201 on the catheter 124 are predetermined, the position of the catheter 124 may be determined.

The position data of the catheter 124 is used in conjunction with volume data or other image data of the patient 112 to create a 3D or virtual image of the catheter 124 during or after the medical procedure. For example, the imaging system 100 or a separate imaging system gathers image data of an area of the patient 112 associated with the positioning of the catheter 124. The image data may be obtained during or before the medical procedure involving the catheter 124. Based on the image data, a 3D image is generated. Any known or future image construction technique may be utilized. For example, volume rendering (including voxel arrangement, coordinate transformation, ray casting, and lighting calculations), surface rendering, image mesh techniques, and/or any other mathematical or digital signal processing method for generating 3D images is used. The position data of the catheter 124 is superimposed or combined with the 3D image of the internal area of the patient 112 to allow a medical professional view a virtual catheter during or after the medical procedure.

Also, changes in position of internal anatomy based on a heart, breathing, or other physiological cycle may impact the positions of the catheter 124, the reference catheters 128, and/or the body surface electrodes 130. To limit effects of physiological cycles, the imaging system 100, another imaging system, and/or the electrode system 120 generates a physiological cycle waveform. The cycle or a portion thereof is used for triggering purposes when electrical characteristic measurements between electrodes are acquired. Alternatively, motion artifacts are corrected by creating a 4D motion function of the electrodes by filming an image sequence, such as an X-ray image sequence, through one heart beat or respiration cycle. Within each cycle, each electrode is given a 3D coordinate for each frame by image segmentation. The electrodes will then be described by a position function. For example, electrode position=f(x(t), y(t), z(t)), where f is a function in three dimensional space. Once f has been derived, the position in each X-ray frame is correlated to a certain timestamp during the physiological cycle. The timestamp information is synchronized with the motion of the electrodes, and, therefore, the motion artifacts may be removed.

Any or all of the data generated by the catheter 124, the reference catheters 128, the body surface electrodes 130, the imaging system 100, and/or the electrode system 120 is stored in the memory 140 and/or 130. Additionally, instructions executable by the processor 102 and/or 130 are stored in a computer-readable medium, such as the memory 106 and/or 140. The instructions implement the methods, acts, and processes described above. The instructions for implementing the processes, methods and/or techniques discussed above are provided on computer-readable storage media or memories, such as a cache, buffer, RAM, removable media, hard drive or other computer readable storage media. Computer readable storage media include various types of volatile and nonvolatile storage media. The functions, acts or tasks illustrated in the figures or described herein are executed in response to one or more sets of instructions stored in or on computer readable storage media. The functions, acts or tasks are independent of the particular type of instructions set, storage media, processor or processing strategy and may be performed by software, hardware, integrated circuits, firmware, micro code and the like, operating alone or in combination. Likewise, processing strategies may include multiprocessing, multitasking, parallel processing and the like. In one embodiment, the instructions are stored on a removable media device for reading by local or remote systems. In other embodiments, the instructions are stored in a remote location for transfer through a computer network or over telephone lines. In yet other embodiments, the instructions are stored within a given computer, CPU, GPU or system. Also, any of the features, methods, techniques described may be mixed and matched to create different systems and methodologies.

Any of the features, components, and methods described above may be mixed and matched to provide for a variety of electrode positioning systems and methodologies. For example, more or less acts may be performed to accomplish the same end of determining a position of the catheter 124.

While the invention has been described above by reference to various embodiments, it should be understood that many changes and modifications can be made without departing from the scope of the invention. It is therefore intended that the foregoing detailed description be regarded as illustrative rather than limiting, and that it be understood that it is the following claims, including all equivalents, that are intended to define the spirit and scope of this invention.

I claim:

1. A method for localizing a catheter, the method comprising:
   providing a catheter electrode, C, and a plurality of reference electrodes, R1, R2, R3, and R4;
   determining distance values between R1 and C, R2 and C, R1 and R2, R3 and C, R4 and C, and R3 and R4;
   identifying first and second triangles based on the distance values between (1) R1 and C, R2 and C, R1 and R2, and (2) R3 and C, R4 and C, and R3 and R4, respectively;
   determining first and second orthogonal distances within the first and second triangles, respectively;
   identifying a first circle having a radius equal to the first orthogonal distance and a second circle having a radius equal to the second orthogonal distance;
   determining a position of the catheter electrode where the first and second circles substantially coincide or are within a minimum distance between the first and second circles;
   applying a transformation to the first and second circles to express the first and second circles in a global coordinate system; and
   displaying an image as a function of the position of the catheter electrode.

2. The method of claim 1, wherein the transformation is an Euler transformation.

3. The method of claim 1, wherein determining the distance values includes determining the distance values based on an impedance or voltage potential.

4. The method of claim 1, further comprising:
   translating origins of the first and second circles to the position of the catheter electrode before applying the transformation.

5. The method of claim 1, further comprising:
   repositioning the first and second circles, after applying the transformation; and
   solving for a global coordinate value of the catheter electrode based on where the first and second circles substantially coincide or the minimum distance between the first and second circles.

6. The method of claim 1, further comprising:
   registering the plurality of reference electrodes in the global coordinate system.

7. A system for localizing a catheter, the system comprising:
   an electrode, C, on a catheter;
   a plurality of reference electrodes, comprising at least reference electrodes R1, R2, R3, and R4, each reference electrode of the plurality of reference electrodes configured to transmit or receive a signal to or from the electrode, respectively; and
   a processor operable to determine distance values between R1 and C, R2 and C, R1 and R2, R3 and C, R4 and C, and R3 and R4, and determine a position of the electrode by identifying first and second circles based on the distance values and applying a transformation to the first and second circles to express the first and second circles in a global coordinate system,
   wherein the electrode is located at a position where the first and second circles substantially coincide or within a minimum distance between the first and second circles, and
   wherein identifying the first and second circles comprises determining first and second orthogonal distances within first and second triangles, respectively, dimensions of the first and second triangles being associated with the distance values between (1) R1 and C, R2 and C, R1 and R2, and (2) R3 and C, R4 and C, and R3 and R4, and the first and second orthogonal distances being the radius for the first and second circles, respectively.

8. The system of claim 7, wherein the transformation is an Euler transformation.

9. The system of claim 7, wherein the plurality of reference electrodes further comprises reference electrodes R5, R6, R7, and R8, and wherein the plurality of reference electrodes comprises six reference electrodes positioned on a body surface and two reference catheter electrodes.

10. The system of claim 7, wherein the processor is operable to determine the distance values based on an electrical characteristic associated with the respective signal.

11. The system of claim 10, wherein the electrical characteristic comprises an impedance or voltage potential.

12. The system of claim 7, wherein the processor is further operable to determine the position of the electrode of the catheter by translating origins of the first and second circles to the position of the electrode of the catheter before the transformation.

13. The system of claim 7, wherein the processor is further operable to determine, after applying the transformation, the position of the electrode of the catheter by repositioning the first and second circles and solving for a global coordinate value of the electrode of the catheter.

14. In a computer-readable medium having stored therein instructions executable by a processor, the instructions comprising:
   providing a catheter electrode, C, and a plurality of reference electrodes, R1, R2, R3, and R4;
   determining distance values between R1 and C, R2 and C, R1 and R2, R3 and C, R4 and C, and R3 and R4;
   identifying first and second triangles based on the distance values between (1) R1 and C, R2 and C, R1 and R2, and (2) R3 and C, R4 and C, and R3 and R4, respectively;
   determining first and second orthogonal distances within the first and second triangles, respectively;
   determining first and second circles based on the first and second orthogonal distances, respectively;
   determining a position of the catheter electrode where the first and second circles are the closest; and
   applying a transformation to the first and second circles, the transformed first and second circles being in a global coordinate system.

15. The instructions of claim 14, wherein the transformation is an Euler transformation.

16. The instructions of claim 14, further comprising:
   translating origins of the first and second circles to the position of the catheter electrode before the transformation.

17. The instructions of claim 14, further comprising:
   repositioning the first and second circles, after the transformation; and
   solving for a global coordinate value of the catheter electrode based on where the first and second circles are the closest.

18. The system of claim 7, further comprising:
a catheter generator configured to generate a first signal having a first signal frequency and transmit the first signal from the electrode on the catheter;
a reference generator configured to generate a second signal having a second signal frequency and to transmit the second signal from a first reference electrode of the plurality of reference electrodes,
wherein the second signal frequency is substantially similar to the first signal frequency but is phase shifted relative to the first signal, such that a current is created between the electrode on the catheter and the first reference electrode.

19. The system of claim 18, wherein the processor is operable to determine the distance values based on a voltage potential difference, created by the current, measured between the electrode on the catheter and the first reference electrode.

20. The instructions of claim 14, wherein determining the first orthogonal distance comprises determining a first shortest distance, $r_1$, between a point between R1 and R2, and the catheter electrode; and
wherein determining the second orthogonal distance comprises determining a second shortest distance, $r_2$, between a point between R3 and R4, and the catheter electrode.

21. The method of claim 1, wherein R2 and R4 represent a same reference electrode.

22. The system of claim 7, wherein R2 and R4 represent a same reference electrode.

23. The instructions of claim 14, wherein R2 and R4 represent a same reference electrode.

* * * * *